United States Patent [19]

Harrington et al.

[11] Patent Number: 4,837,212

[45] Date of Patent: Jun. 6, 1989

[54] TREATMENT OF HEMOLYTIC ANEMIA WITH DANAZOL

[75] Inventors: William J. Harrington; Yeon S. Ahn; Ravindra Mylvaganam, all of Miami, Fla.

[73] Assignee: University of Miami, Coral Gables, Fla.

[21] Appl. No.: 936,957

[22] Filed: Dec. 1, 1986

Related U.S. Application Data

[63] Continuation of Ser. No. 671,786, Nov. 15, 1984, abandoned.

[51] Int. Cl.[4] .............................................. A61K 31/58
[52] U.S. Cl. .................................... 514/176; 514/814
[58] Field of Search ................... 514/176, 184; 540/57

[56] References Cited

U.S. PATENT DOCUMENTS 3,135,743  6/1964  Clinton et al. ........................ 540/57

Primary Examiner—Douglas W. Robinson
Assistant Examiner—Joseph A. Lipovsky
Attorney, Agent, or Firm—Cushman, Darby & Cushman

[57] ABSTRACT

Danazol, a known androgen, is used to (1) correct immune abnormalities associated with hemotologic disorders or (2) treating immune disorders associated with depressed T helper cells, in the invention disclosed.

2 Claims, No Drawings

TREATMENT OF HEMOLYTIC ANEMIA WITH DANAZOL

This is a continuation of application Ser. No. 671,786, filed Nov. 15, 1984, which was abandoned upon the filing hereof.

BACKGROUND OF THE INVENTION

This invention relates to the use of danazol, a known material, in the treatment of hematologic disorders such as paroxysmal nocturnal hemoglobinuria and autoimmune hematologic disorders such as autoimmune hemolytic anemias, secondary immune thrombocytopenias and other blood, cytopenias, and in a method of restoring immune homeostasis in a patient requiring such therapy as well as selected immune deficiency syndromes.

Danazol, known chemically as 17α-Pregna-2,4-dien20-yno[2,3-d]isoxazol-17-ol; 17α-pregn-4-en-20-yno[2,3-d]isoxazol-17-ol; 1-ethynyl-2,3,3a,3b,4,5,10,-10a,10b,11,12, 12a-dodecahydro-10a-12a-dimethyl-1H-cyclopenta[7,8]phenanthro[3,2-d]isoxazol-1-ol; or 17α-ethynyl-17β-hydroxy-4-androsteno[2,3-d]isoxazole; and available as Danocrine from Winthrop Laboratories is a synthetic hormone derived from ethisterone. See British Pat. No. 905,844 (1962 to Sterling Drug), C.A. 58, 689c (1963); and U.S. Pat. No. 3,135,743 (1964 to Sterling Drug). Danazol has the formula.

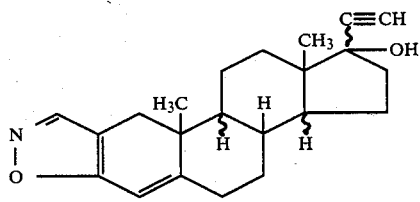

Danazol is classified as an anterior pituitary suppressant and is an androgen which is often prescribed for the treatment of fibrocystic breast disease, endometriosis and hereditary angioedema. Danocrine ® brand of danazol is available in 50, 100 and 200 mg. capsules. See Merck Index, 12th Edition, monograph 2799 (1983).

The treatment of idiopathic thrombocytopenic purpura (ITP) with danazol is reported by the present applicants and others in the June 9, 1983 edition of the New England Journal of Medicine 308:1396–1399 at an oral dosage rate of 200 mg. two to four times a day. ITP is an autoimmune disorder, most common in young women, in which platelets react with an auto-antibody and are destroyed by macrophages. There is no known underlying disease causing thrombocytopenia in ITP.

Prior methods of therapy for autoimmune disorders include the use of glucocorticoids, which have potentially serious side effects such as osteoporosis, infections, diabetes mellitus, complications often unavoidable over periods of prolonged use. The use of danazol or other androgens as a partial or complete replacement for glucocorticoids will minimize and in some cases prevent these serious side effects as well as reduce the amounts of glucocorticoids required for effective therapy.

SUMMARY OF THE INVENTION

Danazol as an immune modulator

Our further studies have revealed that danazol, and probably other related androgens, act as immune modulators, correcting immune abnormalities associated with autoimmune.

The amount of danazol effective to achieve the result desired varies depending upon the condition treated, general health, sex and age of the patient, as well as other factors, and is determined by the clinician on an empirical basis.

The human immune system consists of discrete subsets of T cells critical for immune homeostasis. The inducer/helper cell (Th) plays a central role in the activation of other T cells, B cells and macrophages, thus amplifying immune responses and this inductive response is regulated by another subset of suppressor/cytotoxic T cells (Ts). Imbalance of these two subsets leads to a variety of immunologic disorders characterized by autoimmune disorders or immunodeficiency and development of neoplasms.

Recently subset T cell imabalance has been evaluated in many human disorders with monoclonal antibody specific to subset T cell antigens such as OK T4, T8 or Leu 2a, 3a and the ratio of helper/suppressor is often used as an index of immune homeostasis. We have investigated subset T cell alterations in patients with idiopathic thrombocytopenic purpura (ITP), the well defined autoimmune hematologic disease, also known as Werlhof's disease or land scurvy and secondary thrombocytopenia associated with other autoimmune diseases or neoplasms. ITP is a system illness characterized by hemorrhages from the mucous membranes and skin, deficiencies in platelet count and anemia and may be fatal. In this disorder, platelets are sensitized with IgG auto-antibody and cleared through their Fc receptors by macrophages of the mononuclear phagocytic system (MPS). Glucocorticoids and splenectomy are the mainstays of treatment. Recently danazol, a synthetic androgen, was introduced in the treatment of ITP. However, its mechanism of action is unknown.

Subset T cell alterations have been studied in the peripheral blood of patients with idiopathic and secondary thrombocytopenias with, commercially available monoclonal antibodies and studies their modification by danazol therapy. Abnormalities of cell-mediated immunity in ITP have been reported previously: these include blastogenic transformation of lymphocytes to platelet antibody complex, inhibition of leucocyte migration, decrease autologous mixed lymphocyte cultures, impaired lymphocyte transformation to PHA and conconavalin A, and impaired capping of lymphocytes. We found that alteration of subset T cells is frequent in patients with idiopathic and secondary thrombocytopenias and that danazol modulates subset T cell in balances in these disorders.

Forty-six patients (31 females, 15 males) with autoimmune thrombocytopenic purpura (on danazol therapy) of greater than four months duration were studied. Some of these patients were also on low dose glucocorticoids (equivalent to a daily dose of prednisone or 30 mg. or less). Thirty healthy volunteers (20 females, 10 males) were used as controls. Platelet enumeration was with phase-contrast microscopy when there were fewer than 100,000 per ml$^3$ and electronically when there were more. The patient's responses to danazol were classified as excellent when counts rose to 100,000 per cubic millimeter or more for two months or longer; good when they increased to 50,000 but less than 100,000 per cubic millimeter for two months or longer; fair when the level achieved was more than 20,000 but less than 50,000 per cubic millimeter for two months or longer or, at least, doubled the pre-treatment value; and poor when none of the above criteria were met.

Subset T cells were measured at the time of presentation or before danazol therapy and compared to those after danazol therapy. In 10 patients subset T cells were monitored before and between two to 14 weeks during danazol therapy. None of these 10 patients received glucocorticoids. Danazol was given 400–500 mg. a day.

Mononuclear cell preparation: Venous blood (8 ml) was collected in heparin and processed within an hour. The peripheral blood mononuclear cells (PBMC) were obtained by sodium diatrizoate-Ficoll density gradient centrifugate. The PBMC were washed once, counted and $1 \times 10$ cells were placed in each tube. The tubes were centrifuged at 375 g for 10 minutes to pellet the PBMC and the supernatant was discarded.

Monoclonal antibodies: The monoclonal antibodies used in this study (Leu 4, Leu 3a and Leu 2a; Becton Dickinson, Mountain View, California) have been defined. Leu 4 (Pan T) reacts with 80% to 95% of peripheral blood lymphocytes (PBL) that form rosette with SRBC and 65% to 85% of thymocytes. Leu 3a (Th) reacts with 35% to 55% of PBL and identifies helper-/induced T subset. Leu 2a (Ts) binds to 20–36% of PBL and identifies the suppressor/cytotoxic T subset.

Direct immunofluorescence staining: The fluorescein conjugated monoclonal antibody (5ul) was added to the PBMC cell pellet ($1 \times 10^6$). The contents were gently resuspended and incubated at 4° C. for 40 minutes. Then 1 ml of phosphate buffered saline (PBS) was added and centrifuged at 375 g for 10 minutes. The supernatant was discarded and this working procedure repeated twice. The PBMC were finally resuspended in 2 ml of PBS and prepared for flow cytometric measurement. For non-specific background staining a fluorescein conjugated mouse $IgG_1$ was used.

Flow cytometric analysis: The PBMC were passed through an EPICSV (Coulter Electronics, Hialeah, Fla.). The percentage of auto and non-specific fluorescence was consistently less than 1% and 2%, respectively. The monocyte contamination of the lymphocytes (using the Leu-M3 antibody), was similarly less than 2%.

Statistics: The two sample students T test and paired test were used to analyze the results.

RESULTS

FIG. 1 summarizes subset T cells in patients with autoimmune thrombocytopenia. Subset data with and without danazol therapy were compared with those of sex matched controls. Among 52 patients with autoimmune thrombocytopenias (idiopathic and secondary) studied, more than half were found to have abnormal subset T cells with depressed Th/Ts ratios. Compared to controls, most patients with autoimmune thrombocytopenias showed statistically significant low T11 ($P<0.005$), low T4 ($P<0.00005$) and low Th/Ts ratio ($P<0.0005$). In excellent/good/fair/poor responders Pan T cells (T11) recovered toward normal with danazol therapy. Recovery of T helper was more complete in excellent responders compared to good/fair/good responders. Recovery of Th/Ts ratios were noted in both groups.

Immunologic alterations do not appear to be influenced by factors such as the use of low dose glucocorticoids, splenectomy, duration or severity of disease. However, most patients with prolonged remissions of their disease without maintenance therapy have normal subset T cell ratios which suggests that a normal ratio may be an important factor to sustain remission in autoimmune thrombocytopenias. FIG. 2 summarizes serial monitoring subset T cells on 10 patients treated with danazol alone. Alterations of subset T cells by danazol therapy were analyzed within one month to 10 weeks after therapy. Within a month danazol increased the percentage of T helper cells (Th) ($P<0.002$). Therefore, the increased ratio Th/Ts ($P<0.005$). These changes were pronounced after 10 weeks with increased percentage of Th (0.0004) and total Pan T cells ($P<0.05$), and further increase in Th/Ts ratios ($P<0.0002$).

When absolute numbers of subsets were monitored danazol increased absolute number of helper Th cells in four weeks ($P<0.05$) and after 10 weeks, further increases in helper T ($P<0.05$) and Pan T ($P<0.05$) were observed. Correction of subset T cell abnormality occurred within four weeks but more complete restoration was observed after 10 weeks of danazol therapy. In both excellent responders and good-poor responders danazol increased $T_4$ and Th/Ts ratios. Even though correction of the T cell subset alteration appears to be better in excellent responders compared to good-poor ones, it is not statistically significant.

In the other seven patients, danazol was administered concomitant with low dose glucocorticoids. Correction of subset T cell abnormality was noted in this group similar to those seen in FIG. 2.

We found that of the 43 patients treated 22 had excellent; 4 good, 9 fair; and 8 poor responses substantiating our earlier observation.

How danazol is able to improve or correct subset T cell abnormalities is not known. We propose the following three hypotheses although we do not wish to be bound to any one theory: (1) danazol might increase lymphokine production thereby increasing helper T cells and increase Th/Ts ratio. (2) danazol might decrease anti-T cell antibody or inhibitors which induce T cell dysfunction or destruction. (3) danazol may induce preferential pooling of Th cells from tissues of specific antibody production to the peripheral circulation, thereby decreasing the stimulus for antibody production.

Our observations indicate that danazol is a novel immune modulator which can be useful in immune disorders associated with depressed T helper cells and reversed Th/Ts ratio. In patients with immune thrombocytopenia associated with other autoimmune disorders, acquired immune deficiency syndrome (AIDS), and neoplastic disorders, especially lymphomas, leukemias and myelomas, danazol improved the subset T cell abnormality and thrombocytopenia, with clinical improvement.

USE OF DANAZOL IN THE TREATMENT OF HEMOTOLOGIC DISORDERS

Autoimmune hemolytic anemias (AIHA)

Danazol was administered to 10 patients suffering from autoimmune hemolytic anemia (AIHA) of the warm antibody type, an acquired hemolytic anemia due to auto-antibodies that react with the patient's red blood cells. All 10 failed to maintain remission with moderate doses of prednisone; 3 had been splenectomized without benefit, 3 had failed to respond to azathioprine, 3 to cyclophosphamide and 2 to vinca-laden platelets. Danazol was given in doses of 600-600 mg. daily.

In 3 patients, it was possible to stop prednisone completely and remission was maintained for 4 months to 2 years with danazol. In the patients the concurrent administration of glucocorticoids was required, but in all it was possible to decrease the dose of glucocorticoids by 50% or more. Decreases in titers of both IgG and C3 were observed. The decrease in C3 was more pronounced than in IgG, suggesting that inhibition of complement activation might be the mechanism of action of danazol. Danazol was effective regardless of duration of illness, age or sex of the patient, severity of disease or outcome of previous therapy. Based upon our studies, danazol appears to be useful in the management of AIHA of the warm antibody type, both idiopathic and secondary forms.

Three patients with AIHA of cold antibody (cold agglutinin disease) were studied with danazol. Improvement of blood counts and decreased requirement of transfusions were observed with danazol therapy. In one, the addition of tamoxifen enhanced the beneficial effects of danazol.

PAROXYSMAL NOCTURNAL HEMOGLOBINURIA (PNH)

Paroxysmal nocturnal hemoglobinuria (PNH) is an uncommon disorder with a chronic course. Symptoms include intermittent, recurring attacks of hemoglobin in the urine which when present in sufficient quantities cause the urine to be colored varying shades from light red-yellow to fairly dark red.

Both glucocorticoid and androgen therapy have been used with moderate success; however, both are poorly tolerated, especially in women, although the side effects of glucocorticoids can be diminished by alternate day therapy. Iron also is of value but may precipitate crises.

Four patients with paroxysmal nocturnal hemoglobinuria were successfully treated with a combination of iron by mouth and danazol 200 milligrams, three times daily. Two of the patients were women, 33 and 49 years of agent, and two patients, men, 44 and 64 years of age. Their disease had existed for from 4 to 12 years. All required many transfusions, their hemoglobins ranging between 6.4 and 9 grams per decaliter. From previous therapy it was determined that prednisone was poorly tolerated and treatment with intramuscular iron had resulted in only modest improvement.

When treated with danazol and iron by mouth, the hemoglobin levels increased approximately 3 grams in each patient within 3 weeks, and clinical hemoglobinuria largely disappeared. All felt greatly improved and were unwilling to discontinue the danazol therapy for even a brief second control period. The treatment with danazol and iron has been given for 4 to 18 months. None of the patients has had any side effects.

SECONDARY FORM OF AUTOIMMUNE THROMBOCYTOPENIA

Autoimmune thrombocytopenias are often associated with various underlying disorders. These include systemic lupus erythematosus, rheumatoid arthritis, other autoimmune disorders, infections, immune deficiency and neoplasms. Since our publication on its idiopathic form (ITP), we have treated 11 patients with secondary thrombocytopenias: 7 responses were good to excellent. One patient with cyclic thrombocytopenia and two with amegakaryocytic or hypomegakaryocytic thrombocytopenia also responded to danazol.

Our observation indicate that danazol is not only useful to ITP but also effective in secondary thrombocytopenia associated with various underlying diseases.

OTHER HEMATOLOGIC DISEASES

We extended our studies to other hematologic disorders. Patients with anemia, thrombocytopenia associated with myelodysplastic syndrome (refractory anemia), pure red cell aplasia, Felty's syndrome were benefitted with danazol therapy, combined with glucocorticoids.

IMMUNE DEFICIENCY SYNDROMES

Immune deficiency syndromes are either inherited or acquired. We have studied 7 patients with acquired immune deficiency syndrome with danazol combined with other medications such as antibiotics as needed and glucocorticoids intermittently in some patients.

All had severe immune deficiency with reversed subset T-cells ratios. Danazol therapy gradually increased T-cell subset ratios in half of the patients with clinical improvement.

Five patients who had immune thrombocytopenia associated with acquired immune deficiency syndrome were treated with danazol alone. An improvement of platelet count was observed in 3 of 5 patients and in two patients reversed T-cell subset ratios returned to normal.

In one patient with an inherited form of immune deficiency, reversed T-cell subset ratios and thrombocytopenia, danazol improved the platelet count and increased T-cell subset ratios.

Our data indicate the usefulness of danazol as an immune modulator in immune deficiency states, acquired, inherited or associated with other disorders.

We claim:

1. A method of treating autoimmune hemolytic anemia which comprises administering to a person in need of such treatment, an effective amount of danazol.

2. The method of claim 1 in which from 100 to 1,000 mg. of danazol are administered per day.

* * * * *